United States Patent
Tautvydas

[19]

[11] Patent Number: 6,096,533
[45] Date of Patent: *Aug. 1, 2000

[54] MULTI-ZONE STERILITY INDICATOR

[75] Inventor: Kestutis J. Tautvydas, Lake Elmo, Minn.

[73] Assignee: 3M Innovative Properties Company, St. Paul, Minn.

[*] Notice: This patent is subject to a terminal disclaimer.

[21] Appl. No.: 09/261,798

[22] Filed: Mar. 3, 1999

Related U.S. Application Data

[63] Continuation of application No. 08/969,497, Nov. 13, 1997, Pat. No. 5,922,592, which is a continuation of application No. 08/508,594, Jul. 28, 1995, abandoned.

[51] Int. Cl.$^7$ .................................................. C12M 1/34
[52] U.S. Cl. ...................... 435/287.4; 435/287.7; 435/287.9; 435/805
[58] Field of Search ................... 435/31, 287.4, 435/287.7, 287.9, 805

[56] References Cited

U.S. PATENT DOCUMENTS

| | | | |
|---|---|---|---|
| 2,998,306 | 8/1961 | Huyck et al. | 23/254 |
| 3,585,112 | 6/1971 | Ernst | 195/103.5 |
| 3,661,717 | 5/1972 | Nelson | 195/103.5 |
| 3,752,743 | 8/1973 | Henshilwood | 195/127 |
| 4,087,326 | 5/1978 | Kereluk | 195/103.5 |
| 4,245,043 | 1/1981 | Lund | 435/33 |
| 4,252,904 | 2/1981 | Nelson et al. | 435/294 |
| 4,345,028 | 8/1982 | Nelson et al. | 435/30 |
| 4,839,291 | 6/1989 | Welsh et al. | 435/296 |
| 5,073,488 | 12/1991 | Matner et al. | 435/31 |
| 5,252,484 | 10/1993 | Matner et al. | 435/288 |
| 5,366,872 | 11/1994 | Hird et al. | 435/31 |
| 5,536,662 | 7/1996 | Humphries et al. | 435/287.1 |
| 5,922,592 | 7/1999 | Tautvydas | 435/287.4 |

FOREIGN PATENT DOCUMENTS

| | | |
|---|---|---|
| WO 95/08639 | 3/1995 | WIPO . |
| WO 96/06184 | 2/1996 | WIPO . |

OTHER PUBLICATIONS

Article: Hanlon et al., "Quantitative Assessment of Sterilization Efficiency Using Lyophilized Calcium Alginate Biological Indicators," *Letters in Applied Microbiology*, 17, 1993, pp. 171–173.

Article: Dadd et al., "Germination of Spores of *Bacillus subtilis* var. niger Following Exposure to Gaseous Ethylene Oxide," *Journal of Applied Bacteriology*, 60, 1986, pp. 425–433.

Article: Foster et al., "Pulling the Trigger: The Mechanism of Bacterial Spore Germination," *Molecular Microbiology*, 4(1), 1990, pp. 137–141.

(List continued on next page.)

*Primary Examiner*—David A. Redding
*Attorney, Agent, or Firm*—James A. Rogers

[57] ABSTRACT

The present specification describes a sterility indicator device which comprises a container means and a cover means. The container means comprises a plurality of discrete zones, wherein each zone contains biologically active substrate useful in determining the effectiveness of a sterilization process. Each zone is in effect an individual sterility indicator. The device results in increased reliability and accuracy due to the increased number of discrete zones. The number of discrete zones may be of sufficient size so as to provide statistically significant predictive values at the ninety-five percent or better confidence interval for lower numbers of surviving spores.

4 Claims, 2 Drawing Sheets

OTHER PUBLICATIONS

Article: Umeda et al., "Spore Outgrowth and the Development of Flagella in *Bacillus subtilis*," *Journal of General Microbiology*, 118, 1980, pp. 215–221.

Chapter: Pflug et al., "Principles of the Thermal Destruction of Microorganisms," *Disinfection, Sterilization, and Preservation*, Fourth Edition, Chapter 6, 1991, pp. 85–128.

Chapter: Parisi et al.; "Sterilization with Ethylene Oxide and Other Gases," *Disinfection, Sterilization, and Preservation*, Fourth Edition, Chapter 33, 1991, pp. 580–595.

Article: Fred et al., "The Reduction of 2,3,5-Triphenyltetrazolium Chloride by *Pencillium chrysogenum*[1]," *Science*, vol. 109, Feb. 18, 1949, pp. 169–170.

Article: Urban et al., "Nitroblue Tetrazolium (NBT) Reduction by Bacteria," *Acta Path. Microbiol Scand.*, Sect B., 87, 1979, pp. 227–233.

Article: Trevors, "Electron Transport System Activity in Soil, Sediment, and Pure Cultures," *CRC Critical Reviews in Microbiology*, vol. 11, Issue 2, 1984, pp. 83–101.

Article: Stellmach et al., "A Fluorescent Redox Dye. Influence of Several Substrates and Electron Carriers on the Tetrazolium Salt–Formazan Reaction of Ehrlich Ascites Tumour Cells," *Histochemical Journal*, 19, 1987, pp. 21–26.

Article: Rodriguez et al., "Use of a Fluorescent Redox Probe for Direct Visualization of Actively Respiring Bacteria," *Applied and Environmental Microbiology*, vol. 58, No. 6, Jun. 1992, pp. 1801–1808.

Article: Spicher, "Sterilization—The Microbiology Between Claim and Reality," *Zbl. Hyg.*, 194, 1993, pp. 223–225.

Article: Spicher et al., "How Many Biological Indicators Have to be Tested to Make a Reliable Statement as to their Resistance?," *Zbl. Bakt. Hyg.*, I. Abt. Orig. B 179, 1984, pp. 365–380.

Article: LePecq et al., "A Fluorescent Complex Between Ethidium Bromide and Nucleic Acids," *J. Mol. Biol.*, 27, 1967, pp. 87–106.

Article: Prasad et al., "A Simple Fluorometric Method for the Determination of RNA and DNA in Tissues," *The Journal of Laboratory and Clinical Medicine*, vol. 80, Jul.–Dec., 1972, pp. 598–601.

Article: Tautvydas, "Evidence for Chromosome Endoreduplication in *Eudorina californica*, a Colonial Alga," *Differentiation* 5, 1976, pp. 35–42.

Standard: "American National Standard for Biological Indicators for Ethylene Oxide Sterilization Processes in Health Care Facilities," Association for the Advancement of Medical Instrumentation, 1986.

Chapter: Pflug, "Description, Establishment, and Statistical Characteristics of the Endpoint of a Microbial Preservation Process," Chapter 4, pp. 4.1–4.20.

Article: Reich, "Effect of Sublethal Ethylene Oxide Exposure on *Bacillus subtilis* Spores and Biological Indicator Performance," *Journal of the Parenteral Drug Association*, vol. 34, No. 3, May–Jun. 1980, pp. 200–211.

MULTI-ZONE STERILITY INDICATOR

This is a continuation of application Ser. No. 08/969,497 filed Nov. 13, 1997 now U.S. Pat. No. 5,922,592, which is a continuation of application Ser. No. 08/508,594 filed Jul. 28, 1995, now abandoned.

FIELD OF INVENTION

The present invention relates to a multi-zone sterility indicator device for determining the efficacy of a sterilization cycle, where each zone is discrete and effectively a separate biological indicator. This device provides increased reliability and accuracy over indicators currently available. In particular, the present invention provides a multi-zone sterility indicator device having a sufficient number of discrete zones containing bacterial spores such as *Bacillus subtilis* so as to provide statistically significant predictive values at the ninety-five percent or higher confidence interval for lower numbers of surviving spores than is possible with current biological indicators.

BACKGROUND

Biological and chemical indicators used to test and/or determine the efficacy of sterilization processes are well known in the art. Typically, such biological indicators contain microbial spores which are exposed to a selected sterilant or sterilizing process. The survival of any exposed spores is determined by placing the exposed spores in an environment capable of sustaining germination of spores and subsequent growth of the germinated spores. In view of the fact that microbial spores are accepted as being much more resistant to sterilization processes than most other forms of microorganisms, it is assumed that a sterilization process that will kill microbial spores will also kill any other contaminating microorganisms. See, e.g., *Disinfection, Sterilization, and Preservation*, Fourth Edition, ed. Block, Seymour S., Lea & Febiger, Chapter 6 (1991) that reports general criteria needed to analyze or assess sterilization processes.

Although cell viability after exposure to a variety of sterilants and/or sterilization processes is a traditional measure of sterility, the effects of such sterilants or sterilization processes on other types of microbial activity have also been investigated. For example, enzymatic activity as described in U.S. Pat. No. 5,252,484 (Matner et al.) and germination rate as described in U.S. Ser. No. 08/196,312 and International Patent Application No. PCT/US95/01984 have also been used to determine efficacy of sterilization processes.

Since sterilization is not uniform throughout a load, the results of spore survival obtained in the least accessible part of a load must be used to determine whether the load was completely sterilized. It is common practice to place only one or two units per point at several different locations of a load of material to be sterilized. The fewer the number of biological indicator units at any one location in a sterilization process, the greater the chance for an erroneous readout of sterilization effectiveness whenever the spore survival is below 100% (based on the number of biological indicator units showing spore outgrowth). The risk of a false readout increases when spore growth periods shorter than seven days are used. Biological indicators are typically tested for accuracy of their readout results in sample sizes about 10 to 200 units per location in a sterilization process for validation purposes in order to attain a confidence level of at least 95 percent. Currently, it is not practical to use this many individual biological indicators per location in a routine sterilization process, particularly since the biological indicators need to be placed in more than one location.

There remains a need for a sterility indicator which will provide a high level of confidence that all parameters necessary to achieve sterilization, including the interrelated parameters of time, temperature and concentrations of moisture, chemicals or radiation dose, have been reached.

SUMMARY

The multi-zone sterility indicator device of the present invention comprises a plurality of discrete zones, with each zone containing at least one biologically active substrate useful in determining the effectiveness of a sterilization process.

In one embodiment, the present invention is a sterility indicator device which comprises a container means and a cover means. The container means comprises a plurality of discrete zones, wherein each zone contains a biologically active substrate useful in determining the effectiveness of a sterilization process. The device results in increased reliability and accuracy due to the increased number of discrete zones, each of which is in effect an independent sterility indicator. The number of discrete zones is of sufficient size so as to provide statistically significant predictive values of the percent survival or percent of zones positive for growth at the ninety-five percent or higher confidence interval for lower average numbers of surviving spores per zone; that is, when approximately only 1 to 30 percent of the zones are positive for growth (0.01 to 0.5 spores, on average, surviving per zone).

In another embodiment, the container means of the device of the invention has substantially liquid-impermeable and substantially non-sterilant absorptive walls. The container means refers to the material forming the framework of the biological indicator of the invention. The container means maintains distinction between the individual zones, to eliminate the possibility of cross-contamination between the zones. The container means also withstands the environments associated with the sterilization process such as high radiation levels in gamma radiation sterilizers or high temperatures encountered in steam sterilizers. Suitable materials include but are not limited to polycarbonate, polyamides, polymethylpentenes and various polyesters. Polypropylene is a preferred material. For certain sterilization processes, a piece of cardboard may suffice as the container means.

The cover means refers to the upper and lower boundaries of the area containing the biologically active substrate (the zone). Typically such cover means are membranes. The cover means is typically porous in order to allow the sterilant to come into contact with the biologically active substrate. When the active substrate is bacterial spores, the cover means also allows the germination/outgrowth medium to penetrate the cover means and contact the spores and is preferably sufficiently translucent to allow determination of bacterial growth/no growth in each zone. Simply put, a preferred cover means is sterilant-transmissive, air-transmissive, light-transmissive, and bacteria-impervious.

It is desirable that the cover means stain little or none with various biological stains, so as to maintain a clear background. At least one of the cover means, the one eventually to be in contact with medium, is hydrophilic in order to draw the medium up into contact with the spores. A particularly preferred cover means is a hydrophilic, porous polycarbonate membrane although other materials such as nylon or hydrophilic polypropylene may also be used.

The other cover means is preferably hydrophobic in order to allow maximum penetration of air during incubation of bacterial spores with suitable growth medium. A preferred cover means is a hydrophobic, porous polypropylene.

The device of the invention results in increased reliability and accuracy over indicators currently used to determine the efficacy of sterilization procedures which are based on direct measurements of growth. The increased reliability and accuracy stems from the decreased error (such as a false negative) encountered with the use of a larger sample size.

Figure 1:
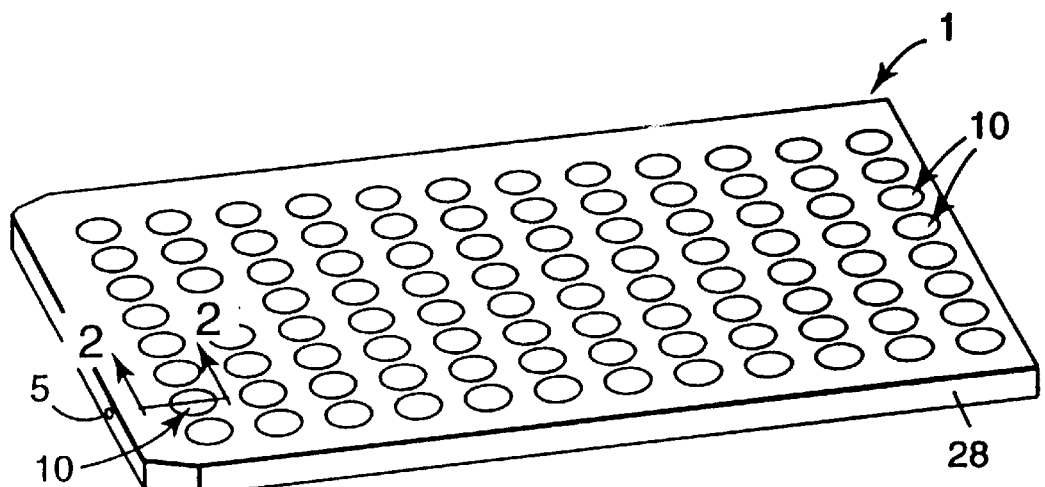
FIG. 1 is an isometric view of a multi-zone embodiment of the sterility indicator device of the invention.

These figures, which are idealized and not to scale, are illustrative and non-limiting.

DETAILED DESCRIPTION OF ILLUSTRATIVE EMBODIMENTS

This invention comprises a multi-zone sterility indicator device. The term "discrete zone" is used to refer to a delineated area containing a biologically active substrate, such as bacterial spores, in such a manner as to allow the biologically active substrate within such zone to contact sterilant and germination/outgrowth medium or water while being entirely separate from other zones. The device results in increased reliability and accuracy due to the increased number of discrete zones, each of which is in effect an isolated independent sterility indicator. This increased number of discrete zones increases the sensitivity, or ability to detect failures, thereby increasing the probability that any negative reading obtained is truly a negative. Thus, fewer partial sterilization cycles will go unnoticed.

Use of the multi-zone sterility indicator of the invention substantially increases the accuracy and reliability of using a biological indicator to monitor the effectiveness of sterilization processes. The use of this multi-zone sterility indicator also allows an earlier readout of results after a sterilization process is completed than is currently possible using direct measurements of growth and still maintain the desired high readout reliability of 97 percent or more in the 30 percent to 80 percent survival range which is a percentage of a biological indicator units positive for growth after 7 days of incubation. Readout reliability is a term used to describe the number of positive biological indicator units observed after exposure to a sterilization process when readings are taken at times shorter than 7 days of growth, as a proportion of the number of positive biological indicator units found after 7 days of growth. Current standards require that, when readings of results are taken at times shorter than the customary 7 days of growth, the number of units showing growth (positive results) should be at least 97 percent of the number of units showing growth after 7 days of incubation. Furthermore, this level of readout reliability must be attained in the 30 percent to 80 percent range of biological indicator units showing growth (percentage of positives for growth after 7 days of incubation).

The following table denotes the required sample size (or number of zones) at the various confidence intervals as a function of the percent survival. The sample size shown is the minimum required to detect at least one zone with growth.

TABLE 1

| Percent Survival | Sample Size | | |
|---|---|---|---|
| | 90% | 95% | 99% |
| 30% | 7 | 9 | 13 |
| 25% | 8 | 11 | 16 |
| 20% | 11 | 14 | 21 |
| 15% | 15 | 19 | 29 |
| 10% | 22 | 29 | 44 |
| 5% | 45 | 59 | 90 |
| 1% | 230 | 299 | 459 |

The number of zones, each of which contains biologically active substrate, is of sufficient number so as to provide statistically significant predictive values at the 95 percent or higher confidence interval. When the biologically active substrate utilized is spores, a pre-determined number of spores (approximately $10^6$ or more per zone, with current standards) is placed into each zone.

Placement of one of the sterility indicator devices of the invention in a given location is the equivalent of placing a number, n, conventional, unitary biological indicators at that location, where n is the number of discrete zones in the sterility indicator device of the invention.

The present device may be used with a variety of methods for determining the effectiveness of a sterilization process. Examples of such methods include quantification of the number of spores, quantification of spore metabolites, determination of a spore germination rates, or methods of allowing cell outgrowth and detecting that outgrowth quantitatively or qualitatively using a variety of dyes that stain cells but not spores, or using substrates that change color or fluoresce when acted upon by the growing cells. The speed of the read-out capability will depend on which method to detect spore outgrowth is used.

The present device may also be used with a variety of sterilization apparatus and techniques. For example, this device may be used to monitor sterilization processes including but not limited to hydrogen peroxide plasma, steam, ethylene oxide, radiation, heat, sodium hypochlorite, polyvinylpyrrolidone-iodine, sodium dichlorocyanurate, low-temperature steam-formaldehyde, glutaraldehyde and hydrogen peroxide or mixtures of these sterilants or processes.

The present invention, although described primarily in terms of a single microorganism species, should be understood to refer as well to the use of a plurality of microorganism species. For example, a single sterility indicator may contain three types of microorganisms, one resistant to heat, a second resistant to gaseous sterilants, and a third resistant to radiation.

One advantage of the present invention over currently used biological indicators is in part the ability to increase the number of biological indicator units in a very small, thin area by several orders of magnitude. Such a multi-zone sterility indicator may easily be placed anywhere in the load to be sterilized. For example, a unit 10 centimeters by 10 centimeters varying in thickness from as thin as 0.25 millimeters (such as the spore card depicted in FIG. 3) to as thick as 1.0 centimeter (such as the device shown in FIG. 1) may contain up to 220 zones.

Another advantage of the present invention is that the biologically active substrate is contained in the individual zones. This containment between two microporous membranes permits the entry of sterilant, nutrient medium, and air, yet prevents the entry of contaminating microorganisms. Since no organisms can enter or leave the zone, the containment also results in a permanent record of the results.

Other advantages of the present invention include the direct exposure of the biologically active substrate to air through the porous membrane. This exposure allows the maximum aeration needed for maximum growth rates. Therefore, a faster readout of results is possible with the sterility indicator of the invention than with biological indicators whose readout is based on growth but where the spores are submerged in the growth medium.

The transparent nature of at least one of the membranes used in the invention allows visual observation of the outgrowth of individual surviving spores into colonies. By counting the colonies, quantitative information about the effectiveness of the sterilization process is obtained. Quantitative information about the effectiveness of the sterilization process is particularly important during the validation of the parameters of the sterilization process. In contrast with current biological indicators, the outgrowth result is either positive or negative. Furthermore, with current biological indicators that are not enclosed, like naked spore strips, it is impossible to determine if the positive result is due to outgrowth of the spores of the indicator organism or from the outgrowth of a contaminant organism accidently introduced during handling of the biological indicators after exposure to the sterilization process. The color or morphology of the visible colonies can distinguish the indicator organism from contaminent organisms.

Referring to the drawings, FIG. 1 is an isometric view of an embodiment of sterility indicator 1. The device contains port 5 into which water or a liquid medium may be injected. This device contains multiple zones 10 each containing at least one biologically active substrate. The container means 28 is made from a suitable material such as polypropylene.

Figure 2:
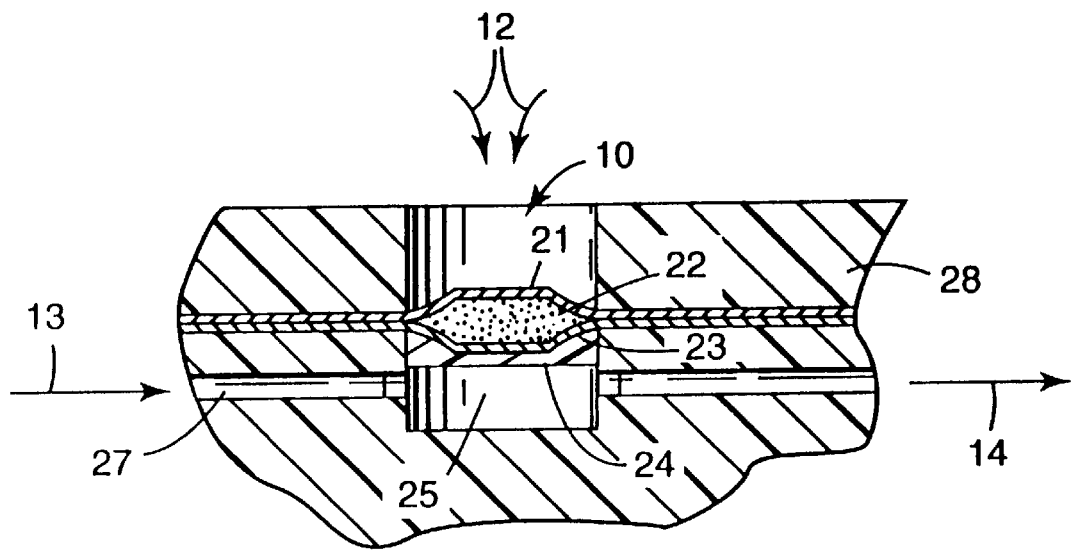
FIG. 2 represents a cross-sectional view of a discrete zone taken along line 2—2 of FIG. 1.

FIG. 2 represents a cross-sectional view of a discrete zone 10 taken along line 2—2 of FIG. 1. Membrane 21 is exposed to the atmosphere, and also defines "zone" 22. Zone 22 contains the biologically active substrate. Hydrophilic membrane 23 is either in contact with or to be contacted by liquid medium 24. Void 25 is an open area through which liquid medium may flow or through which water may flow to wet a dry medium. Casing material 28 covers the areas where the membranes are in contact with each other. Sterilant 12 contacts the exposed membrane. Inlet path 13 and outlet path 14 carry liquid medium or water, and may be plugged to prevent loss of liquid during incubation. In one embodiment, liquid medium flows through void 25, contacting membrane 23. Alternatively, the medium may be a dried medium coated onto the underside of membrane 23. Water flows through void 25, wetting the medium.

Figure 3:
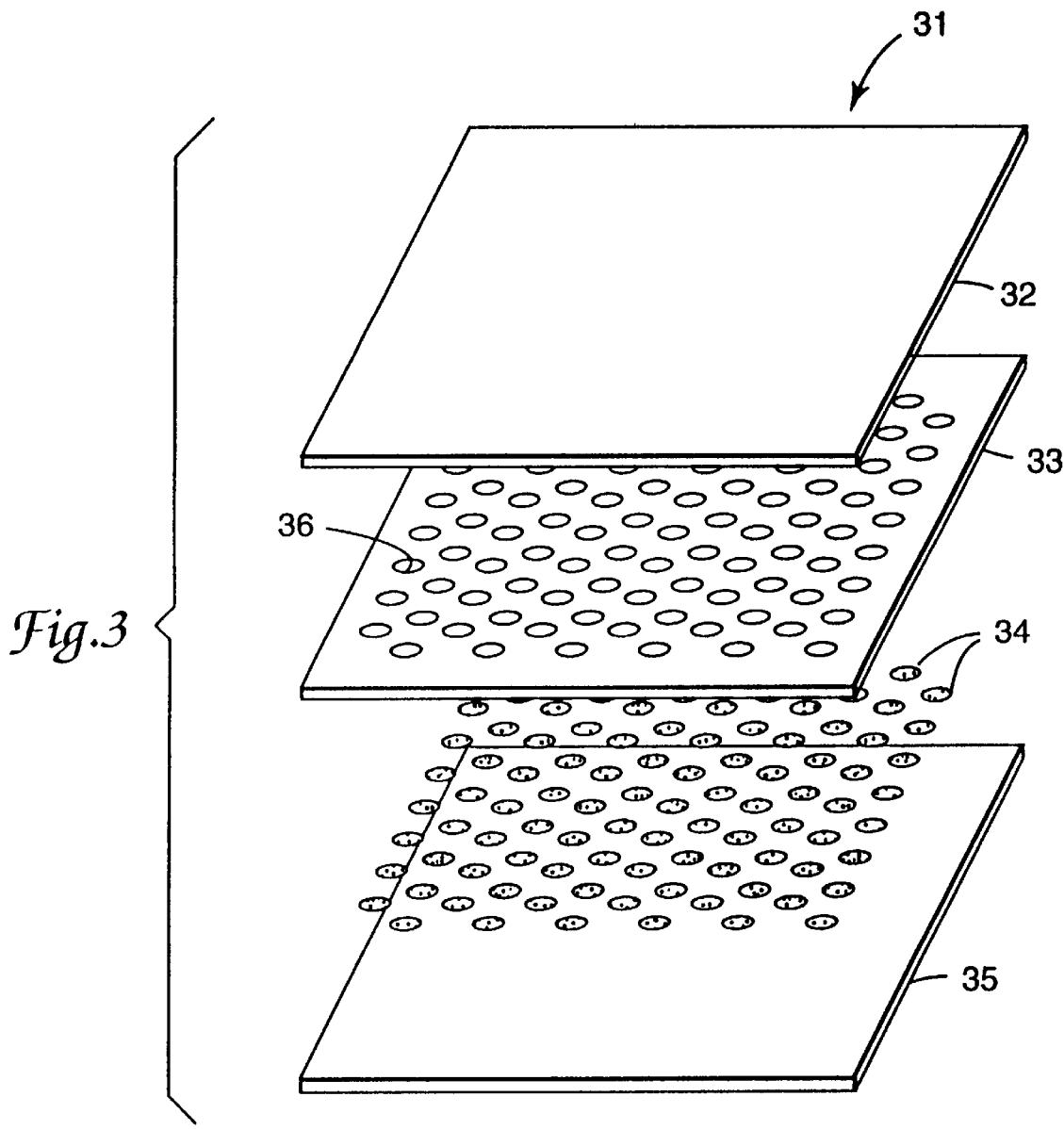
FIG. 3 is an exploded view of a multi-zone strip embodiment of the invention.

FIG. 3 is an exploded view of a strip embodiment indicator 31. 32 represents a porous membrane, 33 represents a piece of double-coated adhesive tape with aperatures 36 punched into it. 34 represents spores in the zones or small circles punched out from a spore-coated filter paper sandwiched between the two porous membranes so that the spores are in the aperatures of the double-coated adhesive tape. Alternatively, 34 could also represent a flat sheet of spore-coated filter paper sandwiched between the two porous membranes using two strips of double-coated adhesive tape. 35 represents a porous membrane.

In a preferred embodiment, device 31 includes bacterial or fungal spores or cells contained between two porous membranes 32 and 35 in a sufficient number of distinct zones so as to be statistically significant. Membranes 32 and 35 are sealed together in such a manner that the small circular aperatures 36, where spores or cells are contained, are left untouched by sealants 33 holding two porous membranes, and a spore-coated filter paper if so used, together. Other methods for establishing separate, non-interactive zones include sonic or electrical welding, heat bonding, or any other suitable method for fusing membranes together while maintaining separate, distinct zones. The membranes 32 and 35 must remain porous above and below the space containing the spores. When used after a sterilization cycle, device 31 is then placed onto a germination/outgrowth medium to germinate and grow the spores. Alternatively, the germination/outgrowth medium may be coated onto the membrane and then dried. Such a strip, now comprising the germination/outgrowth medium, is then placed in contact with water to germinate and grow the spores.

Another preferred embodiment is similar to that described in FIG. 3, with the addition of a polypropylene casing covering the areas where the membranes are in contact. The upper portion of the polypropylene casing has molded aperatures corresponding to the aperatures in the piece of double-coated tape. A dry germination/outgrowth medium, coated onto the hydrophilic membrane, is liquified by the addition of water via an injection port in the polypropylene casing. Alternatively, a liquid medium may be injected through the injection port.

To attain outgrowth of the spores in order to determine the effectiveness of the sterilization process, the sterility indicator device is contacted with a germination/outgrowth medium or water in such a way that hydrophilic cover means 23 is touching the surface of the medium, and cover means 21 is freely exposed to the atmosphere for maximum aeration after exposure to the sterilant. The medium may be optimized for maximum germination and outgrowth rates. A typical medium is of pH 7.3, and contains 10 grams per liter of water (g/L) of glucose, 5 g/L of bacto-casitone, 12 g/L of bacto soytone, 0.2 g/L of L-alanine, and 15 g/L of agar if the spore cards are to be incubated on solidified medium.

When used, after the desired incubation time in contact with the germination/outgrowth medium, the indicator is removed from the medium. A biological stain solution is applied to the spores or cells contained within the zones. After the desired staining time, the stain is rinsed away. Any visible spores that survived the sterilization process and germinated will result in cellular growth which will be stained by the dye. Such dyes are a convenient and accurate means of differentiating cells from spores, because the spores do not stain readily as compared to viable cells with these dyes.

Biological stains or growth-indicator solutions which may be employed in the present invention are well-known in the art and include pH-sensitive dye indicators (such as bromthymol blue, bromcresol purple, phenol red, etc.), oxidation reduction dye indicators (such as methylene blue, triphenyl tetrozolium chloride and its analogs, etc.), and stains that bind to cells more than to spores (such as ruthenium red, safranin, rose bengal, methylene blue, etc.). Such materials typically undergo changes in color in response to a phenomenon of microorganism growth, such as changes in pH, oxidation-reduction potentials, etc. For pH indicators, the period of time required for a single cell or a single spore to produce enough growth so as to acidify the medium and thus change the color of a pH indicator dye can be quite long. The type of medium that may be used with such pH indicator dyes is restricted to those that will allow a pH change. In addition, the change in color can reverse with time resulting in a false reading.

A particularly preferred dye is ethidium bromide, 2,7-diamino-9-phenylphenanthridine-10-ethyl bromide, a fluorescent dye. Its fluorescence is increased substantially (quantum efficiency increased approximately 40 times) upon binding to double-stranded nucleic acids. Ethidium bromide may be used to detect the presence of bacteria and fungi and to quantitate the number of such microbes during growth without having to homogenize the microbes or to extract the nucleic acids.

Fluorescence observed from cells stained with ethidium bromide is a direct measure of the amount of double-stranded nucleic acids present in the cells and thus the number of cells. The ethidium bromide detection system is independent of the metabolic byproducts and the growth medium. Furthermore, the ethidium bromide detection method is more sensitive than the pH indicator approach, and thus should make it possible to detect growth sooner than by other detection methods. For example, it may be possible to detect as few as $10^4$ bacterial cells using ethidium bromide fluorescence. A single undamaged spore of *Bacillus subtilis* can reach this number of cells in six to seven hours. Thus, staining with ethidium bromide is a sensitive method for detection of microorganisms.

EXAMPLES

The invention will be further explained by the following illustrative examples which are intended to be non-limiting.

Example 1

A one-eighth inch Dinker die was used to punch holes in an adhesive tape (3M Scotch™ double-coated adhesive tape #665 available from 3M Company Commercial Office Supply Division, St. Paul, Minn.) to create wells for depositing bacterial spores *Bacillus subtilis*. This punched tape was then placed over a porous polycarbonate membrane (Nuclepore™ membrane available from Costar Corporation through VWR Scientific distributors) which was held in place by applying vacuum through a scintered glass surface. The membrane adhered to the adhesive tape, creating shallow wells into which were deposited a pre-determined approximate number of *Bacillus subtilis* spores in 5 μl of water, using a Gilson Pipetman™ pipetter available through Rainen Instrument Co. Another membrane, a porous polypropylene membrane about 3–5 mils thick with approximately 81% porosity and a pore size no greater than 0.7 micrometers, (such membranes are available through Fischer Scientific), is placed on top of the double-coated adhesive tape so that the two membranes adhere together and covered the spores in the port or well. These spore cards were dried overnight or longer at ambient temperature. The spore cards were then exposed for various lengths of time to ethylene oxide (EtO) in a Josyln-B.I.E.R. vessel at 60% relative humidity, 54.5° C., and 600 mg EtO/liter. The EtO sterilization period was preceded by a 30 minute dwell period at 54.5° C. and 60% relative humidity so as to bring the moisture content of the spores up to the level in the chamber. The spore-outgrowth medium used was water-based solution of pH 7.3 which contained 10 grams per liter (g/L) of glucose, 5 g/L of bacto-casitone, 12 g/L of bacto soytone, 0.2 g/L of L-alanine, and 15 g/L of agar.

The spore cards used contained 22 spore zones each. Eight spore cards were used for each EtO exposure; thus the sample size was 172 spore zones or units per exposure. The results of several trials leading to differing percentages of positive zones are given in Table 2.

The decreased outgrowth of spores in the spore cards with longer exposure to EtO shown in Table 2 demonstrates accessibility and sensitivity of spores in the spore cards to EtO. The rapid outgrowth of spores at the 100% survival level demonstrates that the aqueous media does penetrate the porous membrane, allowing spore outgrowth.

Table 2 also shows that a readout reliability of 97% or higher can be achieved in 48 hours.

TABLE 2

| SPORE-CARD PERCENT READOUT RELIABILITY | | | | | |
|---|---|---|---|---|---|
| HOURS | 100.0 | 96.7 | 80.0 | 68.9 | 38.9 |
| 16 | 71.1 | 60.0 | 28.8 | 20.6 | 8.3 |
| 18 | 90.4 | 84.1 | 63.0 | 40.0 | 19.4 |
| 20 | 93.3 | 88.6 | 68.5 | 57.1 | 50.0 |
| 24 | 97.0 | 93.2 | 89.0 | 73.0 | 66.7 |
| 30 | 97.0 | — | — | — | — |
| 40 | 97.8 | — | — | — | 91.7 |
| 48 | 100.0 | 98.9 | 98.6 | 96.8 | 97.2 |
| 72 | | 98.9 | 98.6 | 98.4 | 97.2 |
| 96 | | 98.9 | 100.0 | 98.4 | 100.0 |
| 120 | | 98.9 | | 98.4 | |
| 144 | | 100.0 | | 100.0 | |
| 168 | | | | | |

Example 2

A one-eighth inch Dinker die is used to punch holes in an adhesive tape (3M Scotch™ double-coated adhesive tape #665 available from 3M Company Commercial Office Supply Division, St. Paul, MN.) to create wells for depositing bacterial spores *Bacillus subtilis*. This punched tape is then placed over a porous polycarbonate membrane (Nuclepore™ membrane available from Costar Corporation through VWR Scientific distributors). The membrane adheres to the adhesive tape, creating shallow wells into which may be deposited a pre-determined approximate number of spores in 5 μl of water using a Gilson Pipetman™ pipetter available through Rainen Instrument Co. Another membrane, a porous polypropylene membrane (such membranes are available through Fischer Scientific), is placed on top of the double-coated adhesive tape so that the two membranes adhered together and covers the spores in the port or well. This structure is then encased in a piece of molded polypropylene with aperatures in the upper polypropylene casing corresponding to the aperatures in the piece of tape. The bottom part of the casing is without aperatures except for a port on the side necessary to introduce medium or water.

This embodiment is particularly useful for tests which are to be performed automatically.

Various modifications and attractions of this invention will become apparent to those skilled in the art without departing from the scope and spirit of this invention.

What is claimed is:

1. A sterility indicator used to determine the effectiveness of an exposure of an article to a sterilant, comprising: a container having a plurality of zones having an upper and lower horizontal barrier, wherein each zone contains at least one biologically active substrate and wherein the upper horizontal barrier is a hydrophobic membrane and the lower horizontal barrier is a hydrophilic membrane.

2. The sterility indicator of claim 1, wherein the container further comprises an inlet pathway and outlet pathway for each zone which provide fluid contact with the hydrophilic membrane.

3. The sterility indicator of claim 1, wherein the hydrophilic membrane is a porous polycarbonate membrane.

4. The sterility indicator of claim 1, wherein the hydrophobic membrane is a porous polypropylene membrane.

* * * * *

UNITED STATES PATENT AND TRADEMARK OFFICE
CERTIFICATE OF CORRECTION

PATENT NO. : 6,096,533
DATED : August 1, 2000
INVENTOR(S) : Kestutis J. Tautvydas It is certified that error appears in the above-identified patent and that said Letters Patent is hereby corrected as shown below:

Column 8,
Line 4, "is" should read -- was --

Signed and Sealed this

Sixteenth Day of October, 2001

Attest:

NICHOLAS P. GODICI
*Attesting Officer*  *Acting Director of the United States Patent and Trademark Office*